(12) United States Patent
Kyriakis

(10) Patent No.: US 9,146,092 B2
(45) Date of Patent: Sep. 29, 2015

(54) MEASUREMENT OF INDUSTRIAL PRODUCTS MANUFACTURED BY EXTRUSION TECHNIQUES

(71) Applicant: Proton Products International Limited, Beaconsfield, Buckinghamshire (GB)

(72) Inventor: John Kyriakis, Beaconsfield (GB)

(73) Assignee: Proton Products International Limited, Beaconsfield, Buckinghamshire (GB)

(*) Notice: Subject to any disclaimer, the term of this patent is extended or adjusted under 35 U.S.C. 154(b) by 0 days.

(21) Appl. No.: 14/140,720

(22) Filed: Dec. 26, 2013

(65) Prior Publication Data

US 2014/0183365 A1    Jul. 3, 2014

(30) Foreign Application Priority Data

Jan. 2, 2013 (GB) .................................. 1300016.1
May 10, 2013 (GB) .................................. 1308415.7

(51) Int. Cl.
*G01J 5/08* (2006.01)
*G01B 11/08* (2006.01)
(Continued)

(52) U.S. Cl.
CPC ................ *G01B 11/08* (2013.01); *G01B 15/02* (2013.01); *G01B 15/025* (2013.01); *G01B 15/045* (2013.01); *G01N 21/3581* (2013.01); *B29C 47/0016* (2013.01); *B29C 47/0021* (2013.01); *B29C 47/0023* (2013.01); *B29C 47/025* (2013.01); *B29C 47/8815* (2013.01); *B29C 47/92* (2013.01); *B29C 47/965* (2013.01); *B29C 2947/92114* (2013.01);
(Continued)

(58) Field of Classification Search
CPC ........... G01J 5/08; G01B 11/08; G01B 15/02; G01B 15/025; G01B 15/045
USPC .......................................................... 250/347
See application file for complete search history.

(56) References Cited

U.S. PATENT DOCUMENTS

| | | | |
|---|---|---|---|
| 3,496,373 A | 2/1970 | Thorman et al. | |
| 3,765,774 A | 10/1973 | Petrohilos | |
| 4,208,126 A | 6/1980 | Cheo et al. | |
| 2002/0067480 A1 | 6/2002 | Takahashi | |
| 2009/0101823 A1 | 4/2009 | Jez et al. | |
| 2011/0046768 A1* | 2/2011 | Rayzak et al. | 700/103 |

(Continued)

FOREIGN PATENT DOCUMENTS

| | | |
|---|---|---|
| DE | 10309845 A1 | 9/2004 |
| DE | 102006048433 | 6/2008 |

(Continued)

OTHER PUBLICATIONS

EP Search Report dated May 13, 2014 of Patent Application No. EP13005999.1 filed Dec. 22, 2013.

*Primary Examiner* — David Porta
*Assistant Examiner* — Hugh H Maupin
(74) *Attorney, Agent, or Firm* — Maine Cernota & Rardin

(57) ABSTRACT

The invention relates to an apparatus for monitoring extruded products moving in an inline extrusion process so as to affect quality control of the process by continuously measuring dimensional parameters and determining the existence of contaminants in the extrusion. The apparatus makes use of Terahertz radiation, which is adapted to provide a curtain of parallel rays of the radiation, which is scanned across the product as the product passes there-through in a linear manner. The composition of the omitted radiation received after the scanning process is subject to an imaging analysis to determine the dimensional parameters and contaminant free integrity of the extrusion process.

10 Claims, 10 Drawing Sheets

(51) Int. Cl.
  *G01B 15/02* (2006.01)
  *G01B 15/04* (2006.01)
  *G01N 21/3581* (2014.01)
  *B29C 47/00* (2006.01)
  *B29C 47/02* (2006.01)
  *B29C 47/88* (2006.01)
  *B29C 47/92* (2006.01)
  *B29C 47/96* (2006.01)
  *G01N 21/88* (2006.01)

(52) U.S. Cl.
  CPC ........ *B29C 2947/92219* (2013.01); *B29C 2947/92228* (2013.01); *B29C 2947/92609* (2013.01); *B29C 2947/92714* (2013.01); *B29C 2947/92723* (2013.01); *G01N 21/8806* (2013.01)

(56) References Cited

FOREIGN PATENT DOCUMENTS

| | | |
|---|---|---|
| EP | 0443322 A2 | 8/1991 |
| EP | 0828143 A2 | 3/1998 |
| EP | 1930714 A2 | 6/2008 |
| EP | 2116838 A1 | 11/2009 |
| GB | 1458594 | 12/1976 |
| GB | 14588828 | 12/1976 |
| GB | 2132343 A | 12/1982 |
| JP | 2002243416 A | 8/2002 |
| JP | 2010261902 A | 11/2010 |
| WO | 2009062315 A1 | 5/2009 |
| WO | 2009117826 A1 | 10/2009 |

* cited by examiner

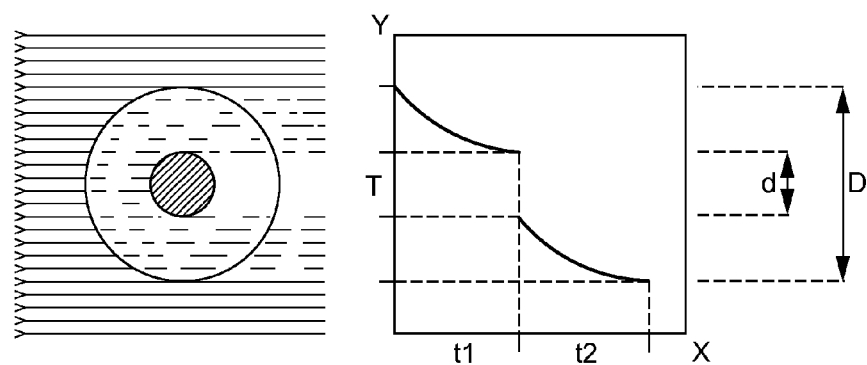
FIG. 7
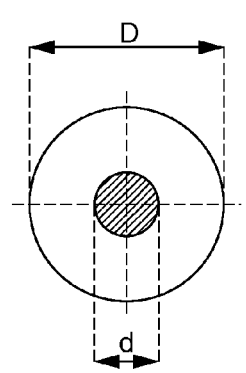
FIG. 8.1
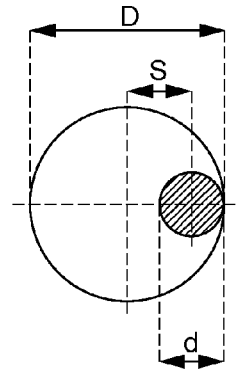
FIG. 8.2

MEASUREMENT OF INDUSTRIAL PRODUCTS MANUFACTURED BY EXTRUSION TECHNIQUES

RELATED APPLICATIONS

This application claims the benefit of Great Britain Application Nos. GB1300016.1, filed Jan. 2, 2013, and GB1308415.7, filed May 10, 2013. Each of these applications is herein incorporated by reference in their entirety for all purposes.

FIELD OF THE INVENTION

The present invention relates to the dimensional properties of elongated linearly extruded products such as rubber or plastic tubing, pipes and electrical cables with metallic conductor cores coated with a non-metallic insulating extruded material as well as manufactured flat products, such as rubber for plastic sheets, insulating tape, films, paper and the like, and more particularly, to an apparatus for the non-contact measurement thereof.

BACKGROUND OF THE INVENTION

Linearly extruded products of the type referred to above are usually manufactured in an extrusion line comprising a pay-off device, an extrusion machine, a cooling section and a take-up device for the completed product.

In continuous manufacturing processes of this type, to which the present invention relates, it is a requirement to measure the diameter and wall thickness of the extruded products, such as tubes or pipes, and, in the case of electrical cables, the eccentricity also, that is the off-set position with respect to coaxiality of the metallic core within the insulating coating of the cables.

The need to monitor these measurements on a continuous basis in an extrusion process is firstly to ensure specification conformity and secondly to ensure that the extruded material is being applied as economically as possible in terms of using only that amount of extrusion material is absolutely necessary, thus avoiding waste.

In the prior art available at the time the present invention was conceived, these measurements were carried out by optical means, using white light or laser light, but these processes are only capable of measuring the overall diameter of the extruded product. By the use of more than one device, it is possible to measure wall thickness and eccentricity indirectly. Ultra-sonic methods have also been used to measure wall thickness, using water as a contact medium.

The use of radioactive beta or x-rays, enables the measurement of the wall thickness of an extruded product without contact with it. However, these methods require special handling by reason of the fact that they involve inherent health hazards as will be readily appreciated.

The invention may also be used in the industrial field of manufacturing flat products, such as, rubber or plastic sheets, insulating tapes, films, paper and the like, thereby to measure the thickness of the material and the overall width of the product being manufactured.

Prior art available in measuring flat products, includes indirect contact methods, whereby two wheels or rollers are placed above and below the product, and the difference of the readings shown by the two wheels, indicates product thickness.

A non-contact optical method has also been used, in which, two "distance measuring devices" are mounted above and below the product. The difference between the two distance readings indicates product thickness.

Both these methods suffer from inaccuracies, which include mechanical wear, wheel bounce in the case of the mechanical contact type, and defocussing on the optical type, either on product vibration or product thickness change.

A further limitation of the "contact" and "optical" methods is that they measure, only the thickness along a narrow part of the product width and not the complete area of the flat product sheet.

Alternative measuring methods such as, Ultrasonic, Radioactive, beta or x-rays are not recommended, since they require special handling and therefore present an inherent health hazard as will be appreciated.

Other representative prior art may be found with reference to:

| | |
|---|---|
| EP0443322 A2 | SUMITOMO ELECTRIC INDUSTRIES |
| GB2132343 A | BHATTACHARY A et al |
| U.S. Pat. No. 3,496,373 A | PHILLIPS PETROLEUM CO |
| U.S. Pat. No. 3,765,774 A | TECHMET CO |
| GB1458594 A | THAELMANN |
| GB1458828 A | DAIDO STEEL CO LTD |
| JP2002243416 A | TOCHIGI NIKON CORP |
| JP2010261902 A | BRIDGESTONE CORP |
| EP1930714 A2 | CANON KABUSHIKI KAISHA |
| DE10309845 A1 | HELM et al |
| US2011/0046768 A1 | RAYZAK |

SUMMARY OF THE INVENTION

It is an object of the present invention, to obviate the problems of the prior art by making use of Terahertz radiation (THz), which does not involve the need for special handling in respect of exposure to the user.

The frequencies of THz radiation are located between infra-red and micro-waves and the wavelengths of THz radiation are in the range between 30 micrometers and 3 millimeters.

Terahertz radiation (THz) has the advantage in that it behaves in a manner similar to that of white light, that is to say that the radiation can be reflected by mirrored surfaces but is able to penetrate and pass through dielectric or insulating materials such as rubber, paper and various plastics including polyethylene and the like.

The speed of transmission of THz radiation through the dielectric or insulating material is dependent on the chemical composition and material density of the product and this property and a penetrative ability of the THz radiation through dielectric or insulated materials will be used to obtain the measurements required in accordance with the invention.

One embodiment of the present invention provides an apparatus for non-contact monitoring of extruded products while moving in an inline extrusion process to determine the dimensional parameters of the products and contaminant free integrity comprising a source of terahertz radiation, means for scanning the product with a curtain of parallel rays of said radiation across the product from one side thereof, detecting means for detecting the composition of emitted radiation on the other side of said product after passage there-through, and means for performing imaging analysis of said emitted radiation thereby to determine said dimensional parameters and contaminant free integrity.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

FIG. 7 shows similar results to those shown in FIG. 6, but in this case measurement is of the overall diameter of an extruded electrical cable and the diameter of the cable core.

FIG. 8 shows the cross section of a moving cable in which in FIG. 8.1 the core of the cable is travelling concentrically and in FIG. 8.2 the cable is non-concentric, which positional eccentricity can be measured in accordance with embodiments of the present invention.

DETAILED DESCRIPTION

Preferred embodiments of the invention are shown in FIGS. 1-16 to which reference will be made in the following discussion.

Where similar parts of the apparatus to be described are used throughout the drawings, these will be referred to with identical reference numbers.

Figure 1:
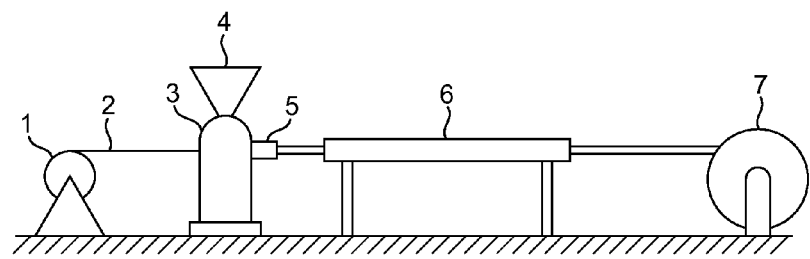
FIG. 1 is a side view of an extrusion line for manufacturing an electrical cable.

With reference to FIG. 1, this illustrates an electrical cable extrusion line comprising a payoff 1 extruding a metallic conductor 2 made of copper, aluminium or steel into an extruder 3.

Rubber or plastic material is introduced into a hopper 4 in the cold state, heated in the extruder 3 which extrudes resulting hot plastics onto the metallic conductor 2 through a forming die-head 5.

The insulated cable is thereafter hauled through a water cooling section 6 and wound on take-up 7.

A non-metallic pipe or tube extrusion line is similar in many respects to a cable line but in which a payoff 1 is not required as the tube or pipe will be formed inside the extruder 3.

Measurement of cable parameters such as diameter/wall thickness and/or eccentricity will take place at positions either before or after the water cooling section 6.

Figure 2:
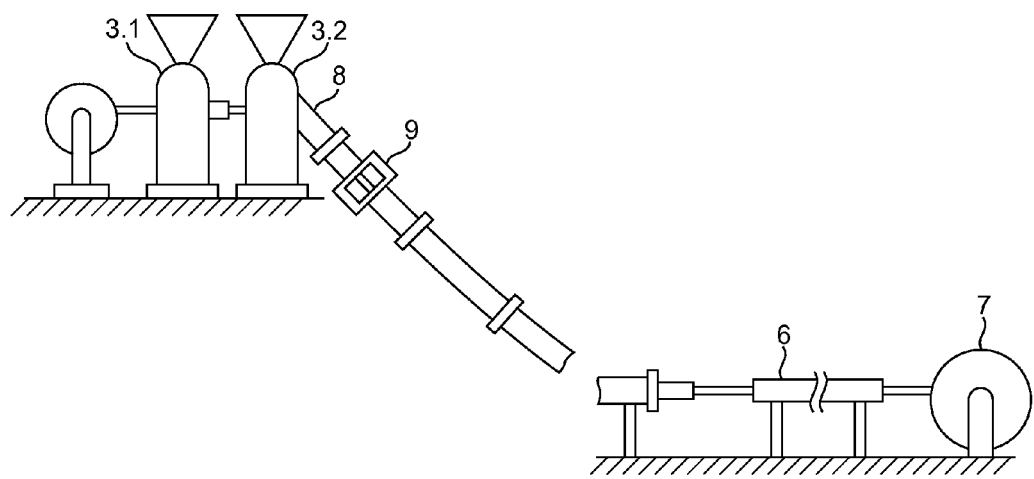
FIG. 2 shows a side view of a double or triple extrusion line for coating the inner metallic core of an electrical cable.

In FIG. 2 there is shown a double or triple extruder line 3.1, 3.2 in which two or three extrusions take place in series and at the same time.

These extrusion lines manufacture electric cables for special applications, such as for use in under sea water communications or high voltage transmission cables.

In the latter case, the cable is extruded in a catenary tube 8 in which the cable installation is heat cured in a steam or nitrogen atmosphere, before it exits into the water cooling section 6 and take-up 7.

Measurements of cable parameters in these lines will take place through a specially constructed 'see through window box 9'.

Figure 3:
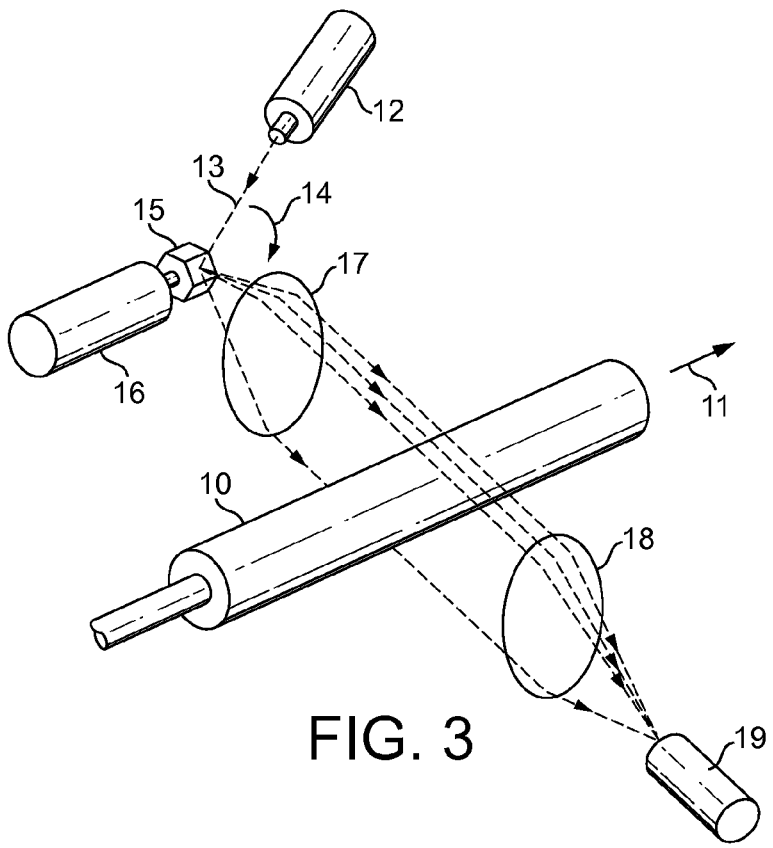
FIG. 3 illustrates the application of an embodiment of the present invention to a tube pipe or electrical cable being extruded in a linear direction along their axes of travel.

To illustrate the employment of the invention in more detail, reference is made to FIG. 3 in which a circular product 10, such as a tube, pipe or electric cable, is shown being extruded in a linear direction along the axis of the product as shown by arrow 11.

A Terahertz (THz) radiating unit 12 provides a ray 13 directed onto a reflecting surface 14.

The reflecting surface 14 is either a single-sided mirror, or one facet of a polygonal mirror drum 15 driven in a rotating manner by means of an electric motor 16.

This rotation in effect scans the ray 13 across the diameter of a lens 17 which produces a curtain of parallel scans of rays across the product 10.

A lens 18, is positioned on the opposite side of the product 10 to receive the THz rays from the lens 17.

A THz sensor 19 and an imaging analysis unit (not shown) analyses the oncoming beams in a manner which will be familiar to one skilled in the arts.

Figure 4:
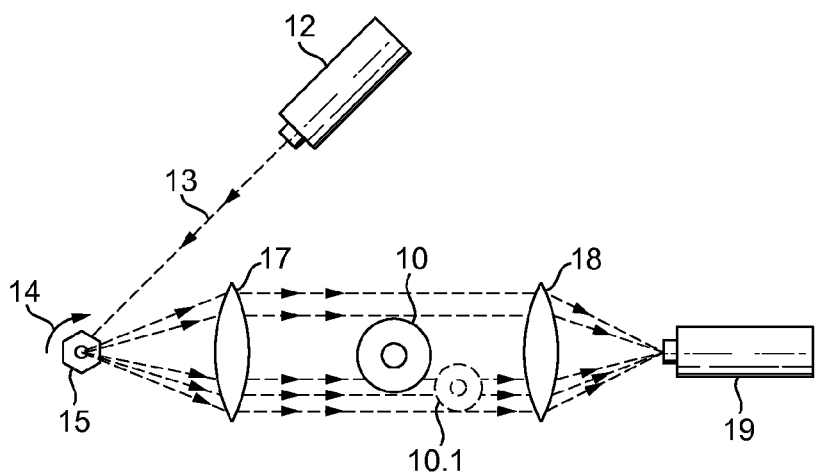
FIG. 4 shows a different view of the arrangement shown in FIG. 3, wherein the travelling product is shown in cross-section to better illustrate how the parallel rays of THz radiation are produced from a single THz radiation source, according to embodiments of the present invention.

FIG. 4 is a cross-sectional view through the travelling object 10 of FIG. 3, to better illustrate the passage of the THz radiation from the unit 12 to rotating mirror 14, 15 the lens' 17, 18 and the THz sensor 19.

As will be evident from FIG. 4 it is possible using the system described, to ascertain the diameter, wall thickness and/or eccentricity of the product 10 in a horizontal plain.

It is also possible as will be readily appreciated to provide a similar arrangement in which measurements may be taken in a vertical plane.

An important reason in accordance with the invention for scanning parallel THz radiation across the product 10 in its path of travel in free space, is that a measurement may take place irrespective of the position of the product 10 within the curtain of parallel rays of THz radiation, see for example position 10.1 of the product shown in FIG. 4.

As alluded to, this method is useful as firstly the product does not have to be guided by contact rollers and secondly, it is important in an application where the object is in a hot state, rendering the same, difficult to guide in any manner or form.

Figure 5:
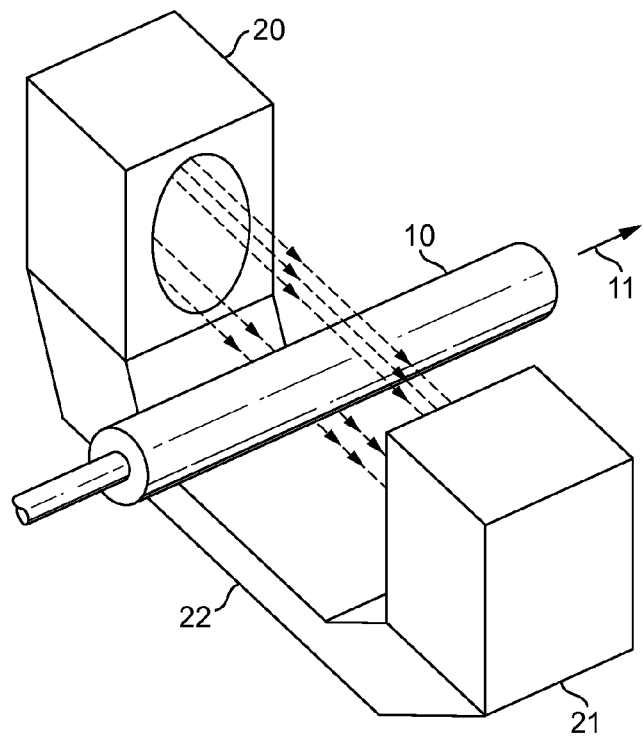
FIG. 5 illustrates, in schematic view, an extruded product, in its path of travel, being subjected to measurements by means of THz radiation, in accordance with embodiments of the present invention.

FIG. 5 shows the product 10 in a position between a transmitter 20 of THz radiation and a receiver 21, mounted on a cradle base 22.

The transmitter 20 houses a THz radiation unit, the motor-driven scanning mirror drum device, 14, 15 and lens 17 shown in previous Figs., thereby to produce a parallel curtain of THz rays across the space between transmitter 20 and receiver 21.

The receiver 21 houses the lens 18, THz sensor 19 and the THz imaging analysis unit circuit, determining the "transit time" of each successive THz ray through the insulating part of the product 10 under test and outputs the values on a processing unit 23 (shown in FIG. 10) which is connected to receiver 21, either by wire or wireless connection.

Figure 10:
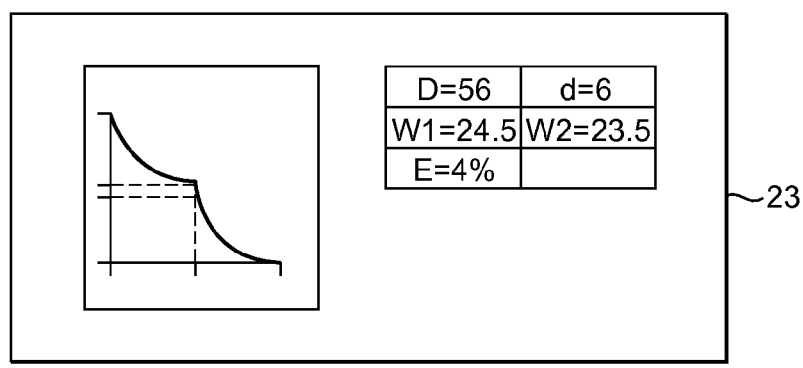
FIG. 10 illustrates a processing unit displaying details of the measurements of an electrical cable under test including a matrix image and values of diameter wall thickness and eccentricity thereof, in accordance with embodiments of the present invention.

The processing unit 23 computes the imaging analysis information and produces matrix images and values of overall diameter (D) inner diameter (d) and eccentricity (E) of the product under test, as shown in FIG. 10.

Figure 6:
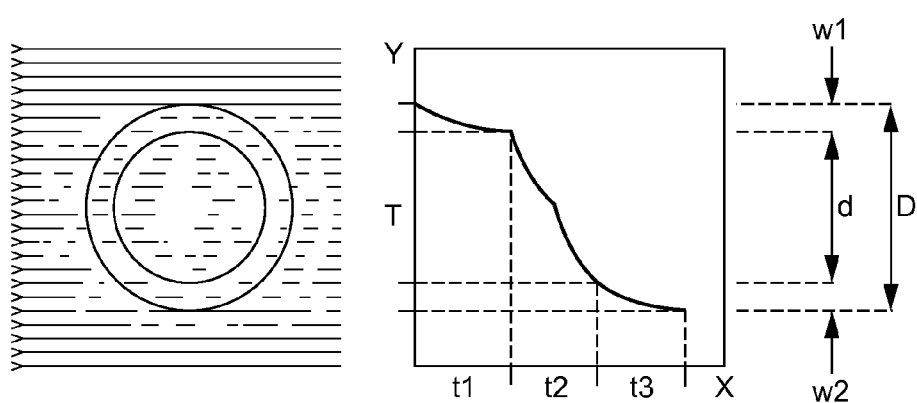
FIG. 6 shows the matrix image of the cross-section of an extruded tube or pipe and in graphical form the results of the measurement of its wall thickness, according to an embodiment of the present invention.

In FIG. 6 the results of measurement of the cross-section of a tube under test is shown in which (D) is the overall diameter (d) is the inner diameter. The horizontal X axis of the graph, displays the "transit times" of the THz radiation t1, t2, t3 and the Y axis of the graph represents the scanning time T.

The wall thickness of the tube is denoted by W1 and W2 in the vertical axis and the average thickness may be computed from the formula (W1+W2)/2=Average Thickness FIG. 7 shows similar results to those shown in FIG. 6 but wherein the cross-section is of a cable in which t1 and t2 are the "transit times" along the axis X of the graphical representation shown and the scanning rate T in the vertical axis Y. (D) represents the overall diameter of the cable and (d) represents the electrical conductor diameter (core) of the cable under test.

FIG. 8 illustrates how the cable eccentricity may be calculated, wherein cable eccentricity may be defined by the equation: E=S/(D/2−d/2)×100%. Where (E) is eccentricity, (D) overall diameter, (d) is core diameter and (S) is distance between the centres of (D) and (d).

In FIG. 8.1 S=0 therefore E=0 which means that the cable is concentric.

In FIG. 8.2 S=D/2−d/2 therefore E=1×100=100% which means that the cable has 100% eccentricity and in practice is unusable.

In a practical example let, D=56 mm, d=6 mm and S=1 mm. Using the eccentricity equation given above, then E=1/25×100%, i.e. 4% which would be an acceptable result. The measurements of (D), (d) and (E) are displayed on the processing unit 23 as referred to above with reference to FIG. 5. Correction of cable eccentricity may be achieved by adjustments to the extrusion forming die-head 5 according to embodiments of the present invention.

Figure 9:
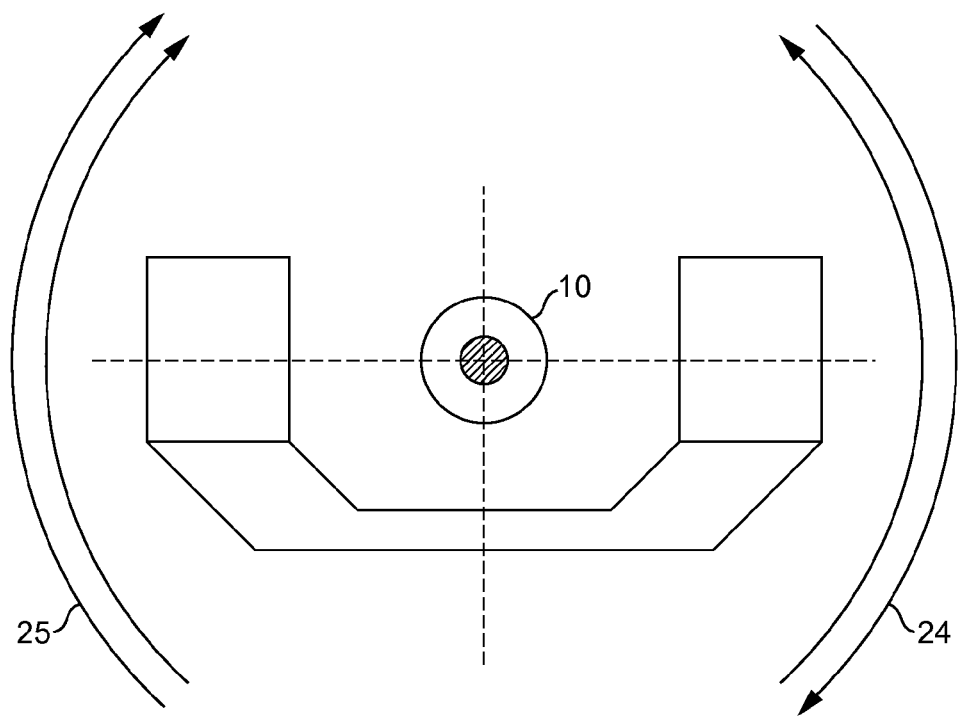
FIG. 9 illustrates a device for obtaining a multiplicity of measurements of the travelling extruded product, in accordance with embodiments of the present invention.

FIG. 9 shows an arrangement wherein the transmitter 20 of THz radiation and the receiver 21 for the radiation after passing through product 10 may be mounted on a rotatable cradle base 22, which is able to perform the following functions. Thus cradle base 22 is able to oscillate about the centre of the travelling product 10 in a "to and fro" rotation and also in a continuous circular mode, illustrated by the arrows 24, 25.

Non-contact transmission from a controller (not shown) to the imaging analysis circuit provided in the receiver 21, permits communication of all functions that are being operated in the receiver 21 as well as the transmitter 20.

The invention as described in the preceding embodiments is able to apply control functions to extrusion lines, whereby by measuring the diameter deviations, feedback can be applied to make adjustments to the extrusion line production speed, in order to maintain the diameter of the cable or tube within required specifications.

In specific cases, the extruder output may also be used for the same purpose. The cable eccentricity may be corrected as referred to already by adjustments to the forming die-head 5, of the extruder 3.

Further preferred embodiments of the invention are shown in FIGS. 11-16.

Figure 11:
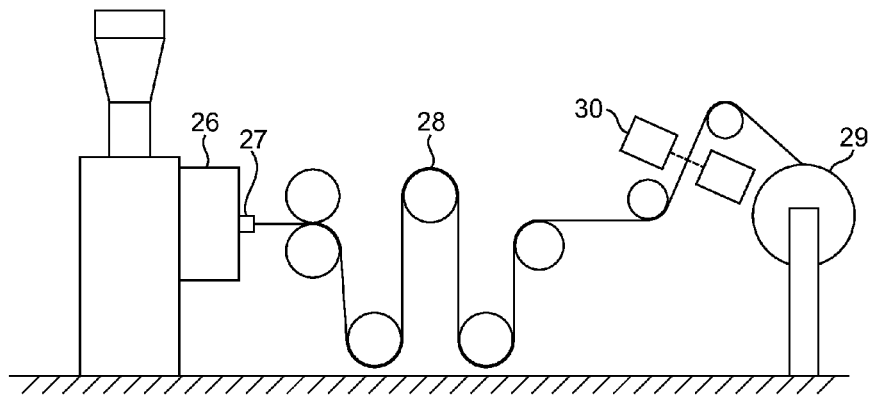
FIG. 11 shows a side view of a plastic extruder similar to the extruder shown in FIG. 1, modified to extrude flat products.

FIG. 11, shows a side view of a plastic extruder 26 similar in operation to the extruder 3 in FIG. 1 but having a modified forming die-head 27, designed to extrude flat sheets of rubber or plastic materials including, polyethylene, nylon, PVC, acrylic and the like, in varying thicknesses and widths.

The hot material exiting from forming die-head 27 enters a cooling zone 28, comprising a number of cooling rolls or calendars, which also determine the thickness of the sheet. The width of the sheet is determined by "side slitters" not shown. The sheet progresses to the take-up 29 and measurements of thickness and width, as well as quality control, may take place in position 30.

Figure 12:
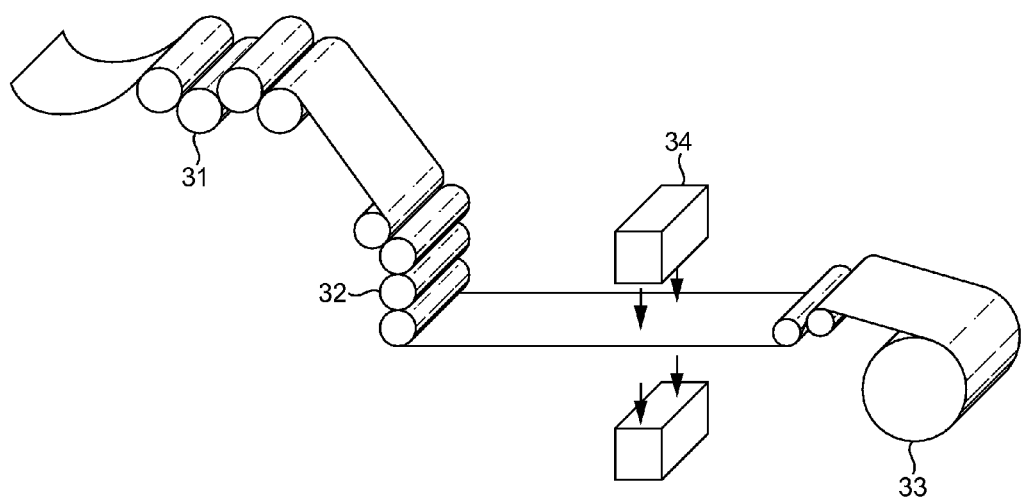
FIG. 12 illustrates a paper sheet producing line.

FIG. 12 shows a "paper sheet producing line" whereby, paper exits from the Pulping Machine (not shown) and enters a drying zone 31 made up from heated drums. Next, the paper moves on to a coating zone 32 thereby it may be coated with various chemicals or plastic materials, depending on application requirements. At this point, the paper is "thickness size" by pressure rollers and the width is determined by "edge slitters" (not shown). The finished paper sheet is wound on to a drum 33 and measurements of thickness and width and quality control, may take place in position 34.

Figure 13A:
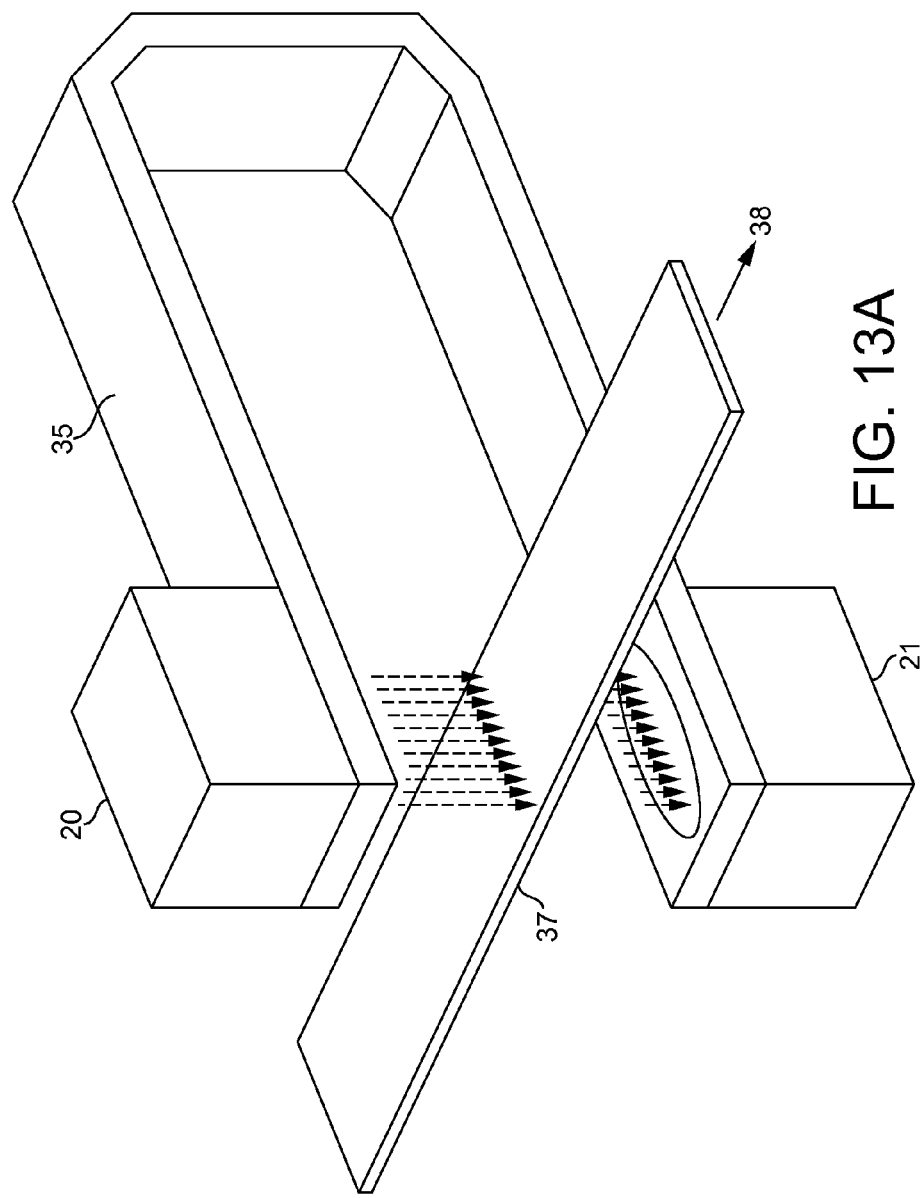
FIG. 13A shows an arrangement similar to FIG. 5, mounted on a C-frame, thereby to continuously scan the complete surface area of a flat product, in accordance with embodiments of the present invention.

FIG. 13A, shows an "installation" of 20/21 transmitter/receiver, FIG. 5 mounted on a C-Frame 35, whereby the curtain of parallel rays of said THz radiation (page 3 lines 9-11) thereof, is scanning continuously the complete surface area of a flat product 37, in its path of travel 38. In this case, the span of the curtain of parallel rays of said THz radiation, is adequately wide, thereby to cope with the full width of product 37.

Figure 13B:
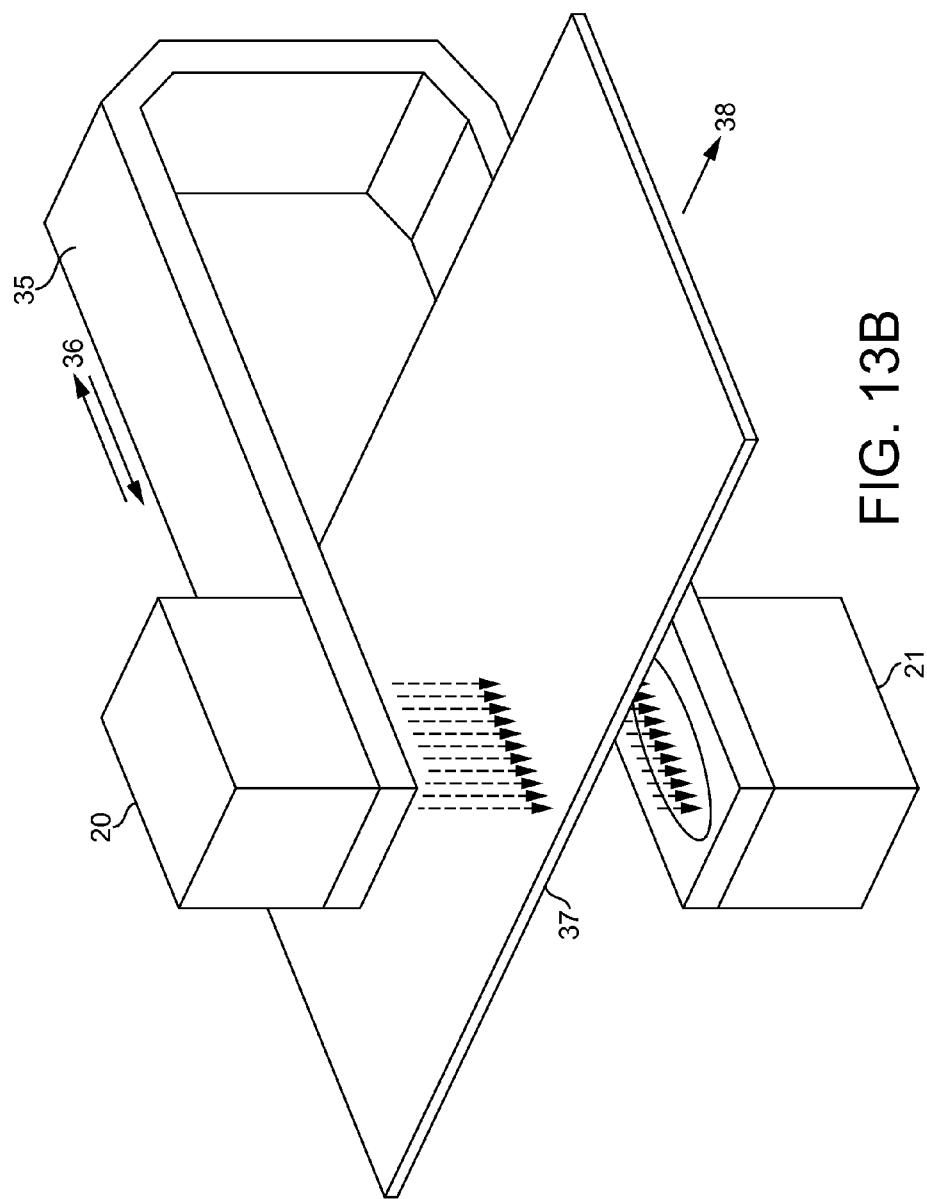
FIG. 13B illustrates the arrangement of FIG. 13A, modified to cater for scanning wide products and provided with a reciprocating motion to achieve that end, in accordance with embodiments of the present invention.

In applications of exceptionally wide products 37, FIG. 13B, it is possible to mount additional said "installations" 20-21 (FIG. 5) on the C-frame (not shown), thereby, to provide, said complete scanning coverage, to the full width of the said product 37 under manufacture, on a continuous basis.

In practice a more economical option may be considered, thereby to provide a single "installation" 20-21 (FIG. 5) on the C-Frame, as it may be adequate, particularly when, the majority of production requirements, are for product widths, which fall within the span of the curtain of parallel rays of said THz radiation.

In some applications processing wide products 37, FIG. 13B, it is possible that intermittent, or random checks of dimensional parameters and or of quality control, are sufficient to ensure minimum acceptable standards for these products. In these cases, a single "installation" 20-21 (FIG. 5) on the C-Frame may be employed, whereby, the said C-Frame is set, in a "Transverse Reciprocating" motion 36, across the width of the product 37, thereby, to facilitate intermittent, or randomized measuring coverage of said product.

Single or multiple "installations" 20-21 (FIG. 5), are connected to the processing unit 23 (FIG. 10), either by wire or preferably by wireless communication, thereby measurements of said product thickness and width, as well as quality control inspection results, are determined by imaging analysis and displayed in a matrix. The processing unit 23 (FIG. 10), can provide complete data logging of several lengths of products, as may be required in cases where high quality is necessary, in the performance and application of said product.

Figure 14:
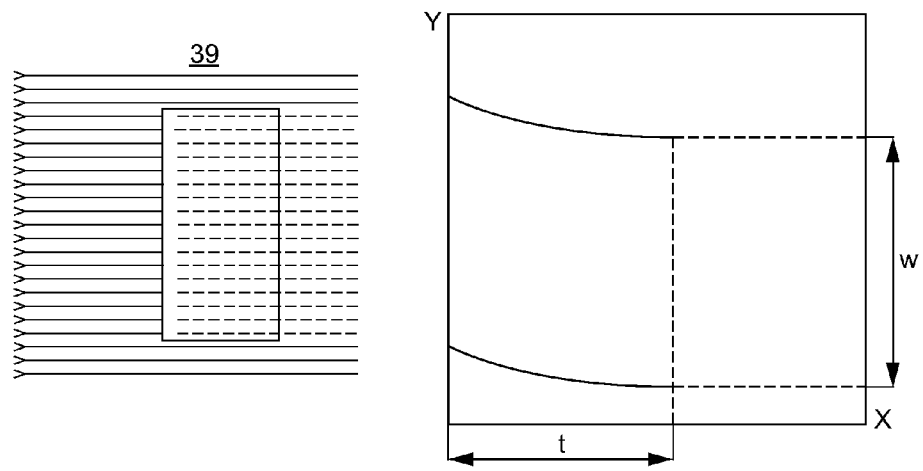
FIG. 14 shows the cross-section of a product under test, together with an associated matrix in graphical format, thereby to provide the imaging analysis of embodiments of the present invention, which provides a measure of the width of the product.

FIG. 14, shows a cross section of product 39 under test, together with the associated matrix in a graph format, whereby the thickness is represented by (t) in the X-axis and the width is represented by (w) in the Y-axis, in a similar manner to the matrix shown in FIG. 6.

Figure 15:
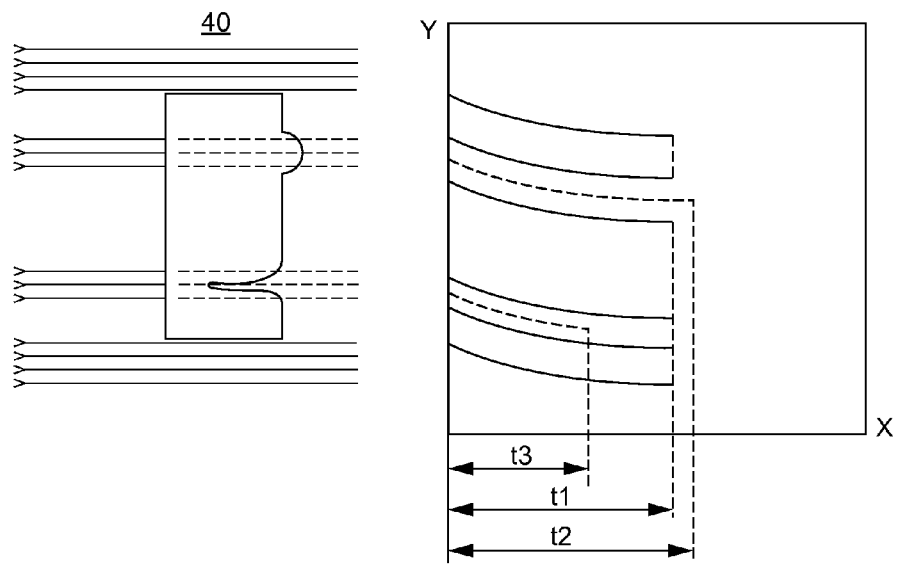
FIG. 15 shows, in graphical display, the resulting analysis of the emitted Terahertz radiation (THz) from the product to provide evidence of ridges or fissures in the manufactured product, in accordance with embodiments of the present invention.

FIG. 15 shows a product 40 with defects. The resulting analysis of the time related signals are displayed in the associated matrix thereof, the X-axis shows ridges as (t2), fissures as (t3) and (t1) as the product thickness.

Figure 16:
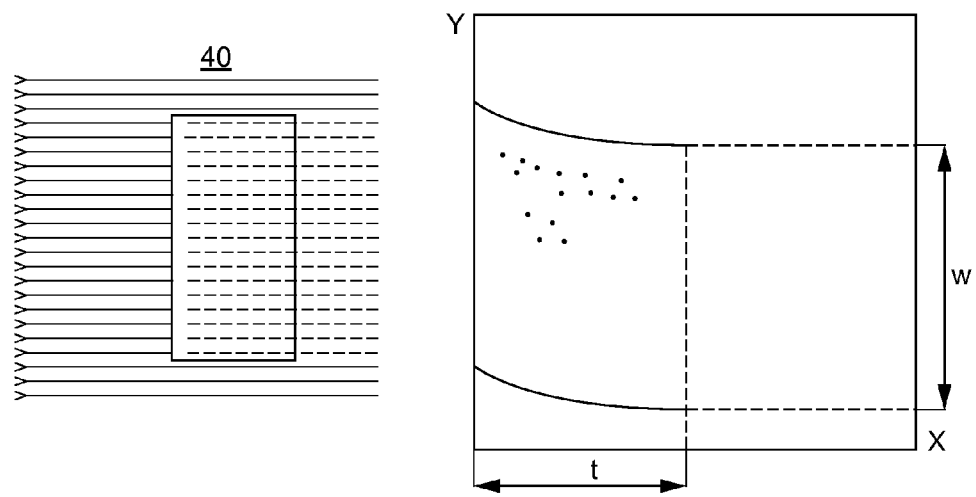
FIG. 16 shows the results of imaging analysis to display contaminants in the finished product such as iron filings or sand particles and the like, in accordance with embodiments of the present invention.

FIG. 16, shows the contaminants in the product, including iron filings or sand particles and the like, displayed as dots in the associated matrix.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. An apparatus for real-time non-contact measurement of the diameter and wall thickness of an elongated, non-guided, industrial product, such as a rubber or plastic tube or electrical cable, being extruded continuously in free space, comprising:
 a terahertz radiation unit;
 a rotating mirror for scanning terahertz rays emitted from a point source across a first lens configured to receive reflective terahertz radiation from said mirror to produce a curtain of parallel terahertz rays, through which the product travels linearly at right angles thereto;
 the said rays after passing through said insulating material being collected by a second lens, and focused at a terahertz sensor; and
 an imaging analyzer for performing time related imaging analysis of terahertz rays penetrating said insulating material to provide a matrix image from which to determine measurement of the diameter and wall thickness of said product in the case of a tube or pipe and/or the eccentricity of its inner core in the case of an electrical cable.

2. The apparatus as claimed in claim 1 wherein the product is coated with a multiplicity of extruded coatings, providing successive wall thicknesses for measurement.

3. The apparatus as claimed in claim 2, including an enclosure or catenary for passage of the product in its path of travel in a hostile environment of high temperature and pressure, said enclosure comprising a transparent window box to allow the passage of the terahertz radiation there-through for measurement in said imaging analysis device.

4. The apparatus as claimed in claim 3, including means for effecting oscillation thereof around the axis of said product in its path of travel to collect a set of data relating to the diameter/wall thickness and/or eccentricity of the product.

5. The apparatus as claimed in claim 4, wherein said oscillation includes either a backwards and forwards motion around the axis of the product, or a continuous rotational mode around the product, to log a set of data relating to the diameter, wall thickness and/or eccentricity of the product under test.

6. The apparatus as claimed in claim 1, wherein means are provided for applying a corrective action to the extrusion line to vary the production speed, extruder volume output and/or adjustment of the forming die-head of the extruder either automatically or manually, in order to maintain a predetermined required product specification.

7. The apparatus as claimed in claim 1, wherein the curtain of parallel rays of said terahertz radiation is used to scan a flat product, which is equal or less in width to the span width of the curtain of parallel rays of terahertz radiation, in order to inspect the complete area of the said product.

8. The apparatus as claimed in claim 7, wherein such apparatus is mounted on a C-Frame, and adapted to move reciprocally, in a transverse manner, at right angles to the linear path of travel of the elongated flat product, whereby a product wider than the width span of the said curtain of parallel rays of terahertz radiation, may be scanned, by moving the C-Frame in a reciprocating forward and reverse motion across the width of the flat product.

9. An apparatus as claimed in claim 1, wherein storage means are provided for data logging and storing information obtained by said analysis in order to determine the suitability of the product for its intended use.

10. The apparatus as claimed in claim 1 wherein said rotating mirror is a multifaceted mirror, wherein each facet is configured to sequentially receive at least one ray of light from said terahertz unit to produce said planar curtain of terahertz rays.

* * * * *